United States Patent [19]

Gallina

[11] Patent Number: 4,514,384

[45] Date of Patent: Apr. 30, 1985

[54] HEMORRHOID TREATMENT METHOD

[76] Inventor: Damian J. Gallina, 2856 W. 33rd St., Erie, Pa. 16506

[21] Appl. No.: 475,342

[22] Filed: Mar. 14, 1983

[51] Int. Cl.³ .................... A61K 31/56; A61K 31/79
[52] U.S. Cl. ...................... 424/80; 514/171; 514/882
[58] Field of Search ................ 424/80, 240, 338, 322

[56] References Cited

U.S. PATENT DOCUMENTS

| | | | |
|---|---|---|---|
| 1,071,186 | 8/1913 | Stern | 424/322 |
| 1,661,588 | 3/1918 | von Neergaard | 424/322 |
| 2,120,430 | 6/1938 | Rieche | 424/130 |
| 2,143,060 | 1/1939 | Dzialoschinsky et al. | 424/322 |
| 2,430,450 | 11/1947 | Brown | 424/130 |
| 2,436,673 | 2/1948 | Shelton | 424/130 |
| 2,542,898 | 2/1951 | Brown | 424/322 |
| 3,535,422 | 10/1970 | Cox et al. | 424/164 |
| 3,657,413 | 4/1972 | Rosenthal | 424/81 |
| 4,056,611 | 11/1977 | Young | 424/338 |
| 4,075,353 | 2/1978 | Mandy et al. | 424/338 |
| 4,163,800 | 8/1979 | Wickett et al. | 424/326 |
| 4,228,163 | 10/1980 | Bliss | 424/240 |
| 4,268,501 | 5/1981 | Konno et al. | 424/80 |
| 4,291,062 | 9/1981 | Leigh et al. | 424/322 |
| 4,302,441 | 11/1981 | Muhlemann et al. | 424/48 |
| 4,320,116 | 3/1982 | Bjorck | 424/129 |

Primary Examiner—Leonard Schenkman
Attorney, Agent, or Firm—Joseph P. Gastel

[57] ABSTRACT

A method of treating hemorrhoids by applying to hemorrhoidal tissues a composition including by weight carbamide peroxide or benzoyl peroxide in an amount of between about 2% and 40%, polyvinylpyrrolidone in an amount of between about 5% and 70% dissolved in glycerine in an amount of between about 10% and 90%, an anesthetic in an amount of between about 0.5% and 25%, and hydrocortisone in an amount of between about 0.25% and 5%.

15 Claims, No Drawings

HEMORRHOID TREATMENT METHOD

BACKGROUND OF THE INVENTION

The present invention relates to an improved method of hemorrhoid treatment by use of a preparation having cleansing, astringent, antiseptic and healing properties.

By way of background, there are numerous hemorrhoid treatment preparations disclosed in the literature which include compounds for soothing and healing inflamed hemorrhoid tissues. U.S. Pat. No. 2,436,673 discloses the use of suppositories containing zinc peroxide. However, benzoyl peroxide and urea hydrogen peroxide, which is also known as carbamide peroxide and hydrogen peroxide carbamide, are not disclosed in the literature for treatment of hemorrhoids.

In the past, urea hydrogen peroxide has been disclosed for use in oral and otic pharmaceutical preparations (U.S. Pat. Nos. 2,120,430, 3,657,413 and 4,302,441); for use as an antiseptic (U.S. Pat. No. 2,542,898); and for use as an antiseptic when used in combination with glycerol for promoting the healing of damaged tissues (U.S. Pat. No. 2,430,450). Urea by itself has been mentioned for use in suppositories, but not in combination with hydrogen peroxide as a urea hydrogen peroxide compound (U.S. Pat. Nos. 1,661,588 and 4,291,062). Also benzoyl peroxide has been described for use as a skin treatment for such ailments as acne and seborrhea (U.S. Pat. Nos. 3,535,442, 4,056,611, 4,075,353, 4,163,800 and 4,228,163). U.S. Pat. No. 4,320,116 discloses a foodstuff and animal feed stuff containing an antibacterial system and teaches the use of carbamide peroxide for the foregoing purpose. Hydrocortisone is used alone or in synergistic combination in topical and rectal formulations due to its anti-inflammatory, antipruritic and vasoconstrictive action. However, none of the foregoing patents or other prior art known to applicant has ever used urea hydrogen peroxide or benzoyl peroxide either alone or in combination with hydrocortisone in a rectal formulation for hemorrhoid treatment.

SUMMARY OF THE INVENTION

It is accordingly one important object of the present invention to provide an improved method of hemorrhoid treatment by use of a preparation containing either urea hydrogen peroxide or benzoyl peroxide in combination with hydrocortisone for producing a cleansing, debriding, keratolytic, antiseptic, anti-inflammatory, vasoconstrictive, antipruritic, re-epithelization and healing action on rectal tissues.

It is a related object of the present invention to provide an improved method for treatment of hemorrhoids by use of a composition containing hydrocortisone in combination with urea hydrogen peroxide or benzoyl peroxide and a vehicle having a sufficiently high molecular weight so that the vehicle is not adsorbed through the rectal membranes. Other objects and attendant advantages of the prsent invention will readily be perceived hereafter.

The present invention relates to a method of treating hemorrhoids by applying to hemorrhoidal tissues a composition comprising hydrocortisone, and a peroxide selected from the group of urea hydrogen peroxide and benzoyl peroxide in a pharmaceutically effective amount for treatment of hemorrhoid tissues. In its more specific aspects, the foregoing are in a vehicle which comprises a compound having a sufficiently high molecular weight so as not to be adsorbed by the rectal membranes. Also, in its more specific aspects, the preparation contains an anesthetic. The various aspects of the present invention will be more fully understood upon a reading of the following portions of the specification.

DESCRIPTION OF THE PREFERRED EMBODIMENTS

The improved hemorrhoid treatment composition used in the present method comprises urea hydrogen peroxide or benzoyl peroxide, hydrocortisone, an anesthetic and a vehicle. In addition, it may also contain such added items as aromatics and emulsifiers, such as menthol, Polysorbate 80, olive oil, lecithin, and an antifungal or preservative agent, as will appear more fully hereafter. The vehicle may be any one of numerous anhydrous innocuous watersoluble compounds which are commercially available.

The urea hydrogen peroxide, which is also known as carbamide peroxide and hydrogen peroxide carbamide, and which has a formula $CO(NH_2)_2 \cdot H_2O_2$, provides a cleansing and oxygenating action to hemorrhoid tissues. It decomposes to provide epidermal irrigation and desquamation (keratolysis), and produces bacteriostatic activity by way of damaging bacterial proteins. It also inhibits triglyceride (lipid and sebum) hydrolysis, thereby reducing levels of free fatty acid of susceptible duct containing cells that have exits or entries penetrating the epidermis. This tends to decrease inflamation of surrounding tissues or lesions. The production of oxygen also demonstrates a mild astringent activity on injured tissue and, as noted above, hydrogen peroxide exerts a cleansing and debriding action through effervescent activity. The urea aids in solublizing organic debris. The degradation byproducts of urea hydrogen peroxide are harmless and nontoxic if absorbed through the rectal mucosa. The urea hydrogen peroxide can be used in an amount of by weight of between about 2%–40%, and more preferably between about 5%–10%, and most preferably between about 7% and 10%. Benzoyl peroxide may be used in the foregoing amounts in place of carbamide peroxide as the oxygenating agent.

Hydrocortisone (hydrocortisone free alcohol), which has the chemical formula $11\beta$, 17, 21,-trihydroxypregn-4-ene-3,20-dione or $C_{21}H_{30}O_5$, provides a synergistic and additive effect through its vasoconstrictive, anti-inflammatory and antipruritic action. The hydrocortisone (hydrocortisone free alcohol) may be used in an amount by weight of between 0.125%–5%, and more preferably between about 0.5%–2.5%, and most preferably between about 1%–2%. Other hydrocortisone compounds or hydrocortisone salts, such as hydrocortisone-21-acetate ($C_{23}H_{32}O_6$) or hydrocortisone phosphate ($C_{21}H_{31}O_8P$ or 21-hydrocortisonephosphoric acid) or various other topical corticosteroids (glucorcorticoids) may be used on an equivalent weight-weight basis.

The improved composition also includes a topical anesthetic. This compound may be Lidocaine which has the formula $C_{14}H_{22}N_2O$. It is known for use epidurally, topically on mucous membranes and for peripheral nerveblock. Furthermore, it is an accepted safe and effective composition for external rectal use. Being an amide and nonester type of anesthetic, adverse and allegeric reactions to it are rare. Alternate types of anesthetics which can be used are known as dibucaine, dipderidon, benzocaine, tetracaine and pramoxine. The anesthetics may be present in an amount by weight from between about 0.5% to 25%, and more preferably between about 1% and 10%, and most preferably between about 1.5% to 5%.

The vehicle for the urea hydrogen peroxide or benzoyl peroxide, hydrocortisone, and anesthetic is a viscous solution of polyvinylpyrrolidone dissolved in glycerine. Polyvinylpyrrolidone is also known as P.V.P., Povidone and poly[1-(2-oxo-1pyrrolidinyl)ethylene]. It is a white to creamy white odorless powder which is hygroscopic and is soluble in water, glycerol andalcohol. It has a molecular weight of 10,000 to 700,000. Its large molecular weight will prevent absorption through the rectal membranes. P.V.P. has been used as a plasma expander. It can be used in an amount by weight of between 5% and 70%, and more preferably between 20% and 50%, and most preferably between 35% and 50%. Glycerine ($C_3H_8O_3$) which is an accepted emollient, humectant, lubricant and vehicle is safe for internal use. It can be used in an amount by weight of between 10% and 90%, and more preferably between 30% and 70%, and most preferably between 25% and 50%.

The composition preferably also contains a suitable wetting, emulsifying, surfactant and suspending agent. One such agent is known as polysorbate 80 (sorbitan monooleate polyoxethylene). This or equivalent agents can be used in an amount of by weight of between about 1% and 30%, and more preferably between about 2% and 15%, and most preferably between about 5% and 10%.

The composition may also contain olive oil for use as an emulsifying and suspending agent, emollient and pharmaceutical vehicle. The olive oil may be present in an amount of by weight of between about 1% and 20%, and more preferably between about 2% and 15%, and most preferably between about 5% and 10%. Other acceptable oils may be used in lieu of olive oil.

An emulsifier which is safe for internal use is also used. Lecithin is preferred. It may be used by weight in an amount of between about 1% and 20%, and more preferably between about 1% and 10%, and most preferably between about 2% and 7%.

The composition may also contain an antibacterial or antifungal agent, such as methyl p-hydroxybenzoate, benzoic acid and/or acetone sodium bisulfite. Substances of this type are for preventing bacterial or fungal growth. Suitable compounds are known under the trade names of Methylparaben and Propylparaben. The preservative agent may be present by weight in an amount of between about 0.1% and 2%, and more preferably between about 0.1% and 1%, and most preferably between about 0.25% and 0.75%.

Actual preparations have been formulated according to the following examples wherein the ingredients are listed in percentages by weight.

EXAMPLE 1

| | |
|---|---|
| Zinc Oxide | 5.00% |
| Urea hydrogen peroxide | 5.00% |
| Hydrocortisone acetate | 2.0% |
| Polyvinylpyrrolidone | 37.48% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Resorcinol (1,3-benzenediol) | .190% |
| Oil of Eucalyptus | .5% |
| Lecithin | 2.89% |
| | 100.00% |

EXAMPLE 2

| | |
|---|---|
| Urea hydrogen peroxide | 5.00% |
| Hydrocortisone acetate | 1.5% |
| Polyvinylpyrrolidone | 42.98% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Resorcinol (1,3-benzenediol) | .190% |
| Oil of Eucalyptus | .5% |
| Lecithin | 2.89% |
| | 100.00% |

EXAMPLE 3

| | |
|---|---|
| Urea hydrogen peroxide | 7.50% |
| Hydrocortisone alcohol | 2.5% |
| Polyvinylpyrrolidone | 39.48% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Resorcinol (1,3-benzenediol) | .190% |
| Oil of Eucalyptus | .5% |
| Lecithin | 2.89% |
| | 100.00% |

EXAMPLE 4

| | |
|---|---|
| Urea hydrogen peroxide | 10.00% |
| Hydrocortisone alcohol | 1.0% |
| Polyvinylpyrrolidone | 39.17% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Lecithin | 2.89% |
| | 100.00% |

EXAMPLE 5

| | |
|---|---|
| Benzoyl peroxide | 10.00% |
| Hydrocortisone alcohol | 1.0% |
| Polyvinylpyrrolidone | 39.17% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Lecithin | 2.89% |
| | 100.00% |

All of the above formulations were tested on subjects having from moderate to severe hemorrhoid problems and relief from hemorrhoid symptoms was obtained along with actual healing of the tissues.

As noted briefly above, the product can be formulated as a solid, gel, paste, cream, salve, ointment, liquid, and as a powder, depending on the ingredients and amounts used and depending on whether additional fats or solid greases are added.

While preferred embodiments of the present invention have been disclosed, it will be appreciated that it is not limited thereto, but may be otherwise embodied within the scope of the following claims.

What is claimed is:

1. A method of treating hemorrhoids by applying to hemorrhoidal tissues a composition comprising hydrocortisone and a peroxide selected from the group of urea hydrogen peroxide and benzoyl peroxide in pharmaceutically effective amounts for treatment of said hemorrhoidal tissues.

2. A method of treating hemorrhoids as set forth in claim 1 wherein said composition includes a vehicle and wherein said peroxide is present by weight in an amount of between about 2% and 40% and said hydrocortisone is present in an amount of between about 0.125% and 5%.

3. A method of treating hemorrhoids as set forth in claim 1 wherein said composition includes a vehicle and an anesthetic.

4. A method of treating hemorrhoids as set forth in claim 3 wherein said peroxide is present by weight in an amount of between about 2% and 40%, and wherein said hydrocortisone is present by weight in an amount of between about 0.125% and 5%, and wherein said anesthetic is present by weight in an amount of between about 0.5% and 25%.

5. A method of treating hemorrhoids as set forth in claim 1 wherein said composition includes a vehicle of polyvinylpyrrolidone.

6. A method of treating hemorrhoids as set forth in claim 5 wherein said polyvinylpyrrolidone is present by weight in an amount of between about 5% and 70%, and wherein said peroxide is present by weight in an amount of between about 2% and 40%, and wherein said hydrocortisone is present by weight in an amount of between about 0.125% and 5%.

7. A method of treating hemorrhoids as set forth in claim 6 wherein said polyvinylpyrrolidone is dissolved in glycerine.

8. A method of treating hemorrhoids as set forth in claim 7 wherein said glycerine is present by weight in an amount of between about 10% and 90%.

9. A method of treating hemorrhoids as set forth in claim 8 wherein said composition includes an anesthetic present by weight in an amount of between about 0.5% and 25%.

10. A method of treating hemorrhoids as set forth in claim 1 wherein said composition includes a vehicle of polyvinylpyrrolidone dissolved in glycerine.

11. A method of treating hemorrhoids as set forth in claim 10 wherein said peroxide is present by weight in an amount of between about 2% and 40%, and wherein said hydrocortisone is present by weight in an amount of between about 0.125% and 5%, and wherein said polyvinylpyrrolidone is present by weight in an amount of between about 5% and 70%, and wherein said glycerine is present by weight in an amount of between about 10% and 90%.

12. A method of treating hemorrhoids as set forth in claim 9 wherein said composition includes a wetting agent, a suspending agent, an emulsifying agent, and a preservative.

13. A method of treating hemorrhoids as set forth in claim 11 wherein said composition includes a wetting agent, a suspending agent, an emulsifying agent, and a preservative.

14. A method of treating hemorrhoids as set forth in claim 11 wherein said composition includes an anesthetic present by weight in an amount of between about 0.5% and 25%.

15. A method of treating hemorrhoids as set forth in claim 14 wherein said composition includes a wetting agent, suspending agent, an emulsifying agent and a preservative.

* * * * *

UNITED STATES PATENT AND TRADEMARK OFFICE
CERTIFICATE OF CORRECTION

PATENT NO. : 4,514,384
DATED : April 30, 1985
INVENTOR(S) : Damian J. Gallina

It is certified that error appears in the above–identified patent and that said Letters Patent are hereby corrected as shown below:

In the Abstract, line 9, change "0.25%" to --0.125%--.

Column 1, line 29, change "3,535,442" to --3,535,422--.

Signed and Sealed this

Twenty-seventh Day of August 1985

[SEAL]

Attest:

DONALD J. QUIGG

Attesting Officer   Acting Commissioner of Patents and Trademarks